(12) United States Patent
Ku et al.

(10) Patent No.: US 11,767,560 B2
(45) Date of Patent: Sep. 26, 2023

(54) DIAGNOSTIC AND TREATMENT METHOD FOR ENDOMETRIAL CAVITY DISTORTING UTERINE LEIOMYOMA USING MICRORNA

(71) Applicants: Seoul National University R&DB Foundation, Seoul (KR); Korea University Research and Business Foundation, Seoul (KR)

(72) Inventors: Seung Yup Ku, Seoul (KR); Yong-Jin Kim, Seoul (KR); Yoon Young Kim, Seoul (KR)

(73) Assignees: SEOUL NATIONAL UNIVERSITY R&DB FOUNDATION, Seoul (KR); KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 787 days.

(21) Appl. No.: 16/565,443

(22) Filed: Nov. 15, 2019

(65) Prior Publication Data
US 2020/0131575 A1  Apr. 30, 2020

(30) Foreign Application Priority Data
Sep. 10, 2018  (KR) .................. 10-2018-0107960

(51) Int. Cl.
*C12Q 1/6883* (2018.01)
*C12Q 1/6886* (2018.01)

(52) U.S. Cl.
CPC ......... *C12Q 1/6883* (2013.01); *C12Q 1/6886* (2013.01); *C12Q 2600/118* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| 2004/0023910 A1* | 2/2004 | Zhang | ................ C07K 14/475 514/44 R |
| 2008/0182239 A1* | 7/2008 | Mullinax | ............. C12Q 1/6844 435/6.14 |

OTHER PUBLICATIONS

Marsh (Fertil Steril Sep. 1, 2016; 106(3): 766-722).*
Kim (International Journal of Molecular Sciences Aug. 25, 2018, 19, 2524).*
Liang (BMC Genomics 2007 8:166 pp. 1-20).*
Chuang (Endocr Relat Cancer Aug. 2012; 19(4): 541-556).*
Office Action, KR9-5-2019-089427286, Korean Intellectual Property Office, dated Dec. 10, 2019.
Chuang et al., "miR-200c is aberrantly expressed in leiomyomas in an ethnic-dependent manner and targets ZEBs, VEGFA, TIMP2, and FBLN5," Endocrine-Related Cancer, 19:541-556, 2012.
Marsh et al., "Decreased expression of MicroRNA-29 family in leiomyoma contributes to increased major fibrillar collagen production," Fertil Steril, 106(3):766-772, Sep. 1, 2016.
Wu et al., "Effects of miRNA-197 overexpression on proliferation, apoptosis and migration in levonorgestrel treated uterine leiomyoma cells," Biomed & Pharmacother., 71:1-6, 2015.

* cited by examiner

*Primary Examiner* — Amanda Haney
(74) *Attorney, Agent, or Firm* — Gavrilovich, Dodd & Lindsey LLP (57) ABSTRACT

The present invention relates to a method of diagnosing and treating endometrial cavity-distorting leiomyoma using microRNA, and particularly, a composition and a kit for diagnosing uterine leiomyoma, the composition and the kit including an agent capable of detecting a microRNA expression level in a biological sample; a method of diagnosing uterine leiomyoma of a subject, the method including measuring a microRNA expression level in a biological sample from the subject, and diagnosing that the subject has uterine leiomyoma having endometrial cavity distortion or uterine leiomyoma having a likelihood of developing endometrial cavity distortion, when the microRNA expression level is downregulated; and a method of treating uterine leiomyoma, the method including measuring a microRNA expression level in a biological sample from a subject, and performing uterine leiomyoma treatment when the microRNA expression level is downregulated.

5 Claims, 7 Drawing Sheets

Specification includes a Sequence Listing.

SEQUENCE LISTING

```
<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: miR-15b

<400> SEQUENCE: 1
tagcagcaca tcatggttta ca                                              22
```

```
<210> SEQ ID NO 2
<211> LENGTH: 21
<212> TYPE: DNA
<213> ORGANISM: Artificial Sequence
<220> FEATURE:
<223> OTHER INFORMATION: miR-29a

<400> SEQUENCE: 2
tagcaccatc tgaaatcggt t                                               21

<210> SEQ ID NO 3
<211> LENGTH: 23
<212> TYPE: DNA
<213> ORGANISM: Artificial Sequence
<220> FEATURE:
<223> OTHER INFORMATION: miR-29b

<400> SEQUENCE: 3
tagcaccatt tgaaatcagt gtt                                             23

<210> SEQ ID NO 4
<211> LENGTH: 20
<212> TYPE: DNA
<213> ORGANISM: Artificial Sequence
<220> FEATURE:
<223> OTHER INFORMATION: miR-29c

<400> SEQUENCE: 4
tagcaccatt tgaaatcggt                                                 20

<210> SEQ ID NO 5
<211> LENGTH: 22
<212> TYPE: DNA
<213> ORGANISM: Artificial Sequence
<220> FEATURE:
<223> OTHER INFORMATION: miR-197

<400> SEQUENCE: 5
ttcaccacct tctccaccca gc                                              22

<210> SEQ ID NO 6
<211> LENGTH: 23
<212> TYPE: DNA
<213> ORGANISM: Artificial Sequence
<220> FEATURE:
<223> OTHER INFORMATION: miR-200c

<400> SEQUENCE: 6
taatactgcc gggtaatgat gga                                             23
```

DIAGNOSTIC AND TREATMENT METHOD FOR ENDOMETRIAL CAVITY DISTORTING UTERINE LEIOMYOMA USING MICRORNA

CROSS REFERENCE TO RELATED APPLICATIONS

This application claims priority under 35 U.S.C. § 119(a) to Korean Patent Application No. 10-2018-0107960, filed on Sep. 10, 2018, the disclosure of which is incorporated herein by reference.

BACKGROUND OF THE INVENTION

Field of the Invention

The present invention relates to a method of diagnosing and treating endometrial cavity-distorting leiomyoma using microRNA, and particularly, a composition and a kit for diagnosing uterine leiomyoma, the composition and the kit including an agent capable of detecting a microRNA expression level in a biological sample; a method of diagnosing uterine leiomyoma of a subject, the method including measuring a microRNA expression level in a biological sample from the subject, and diagnosing as uterine leiomyoma having endometrial cavity distortion or uterine leiomyoma having a likelihood of developing endometrial cavity distortion, when the microRNA expression level is downregulated; and a method of treating uterine leiomyoma, the method including measuring a microRNA expression level in a biological sample from a subject, and performing uterine leiomyoma treatment, when the microRNA expression level is downregulated.

DESCRIPTION OF THE RELATED ART

Figure 1:
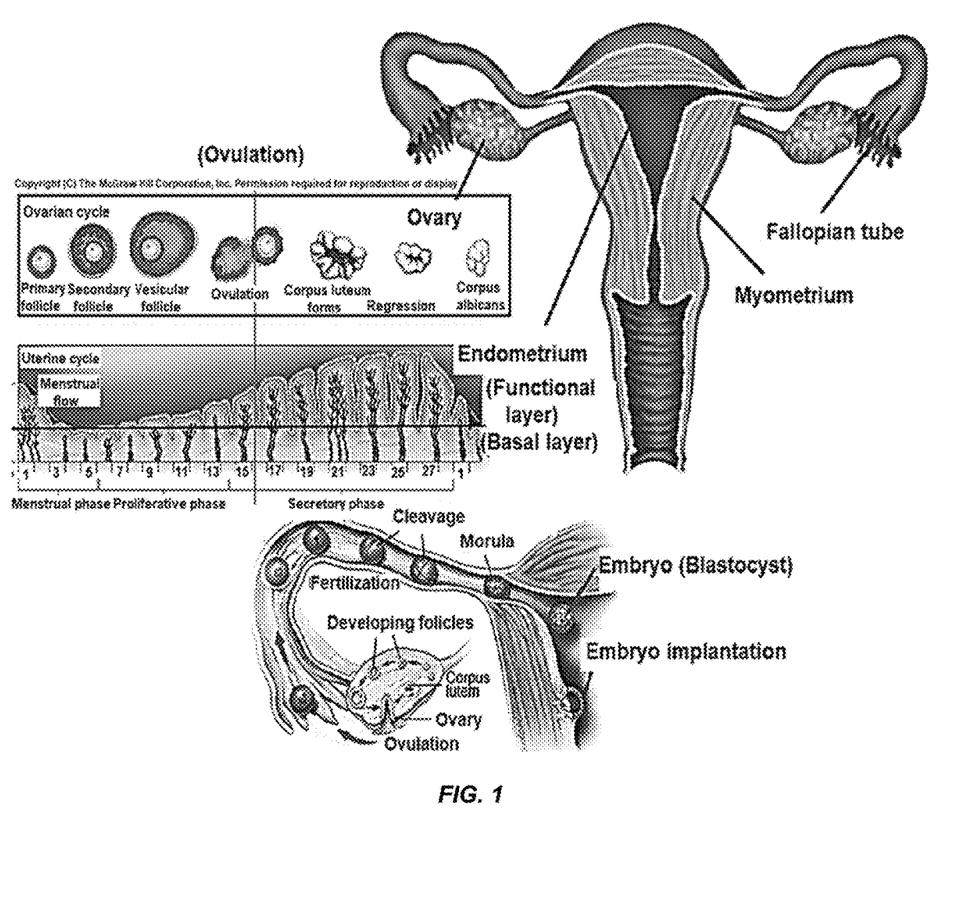
FIG. 1 illustrates the structure and function of the endometrium.

The uterus is a female organ which consists of the uterine body composed of smooth muscles and the endometrium of mucosal tissues; is connected to the vagina in the cervical area; and has ovaries and fallopian tubes as uterine appendages. The uterus functions to induce menstruation in response to hormonal changes according to the ovulation cycle and to maintain pregnancy until delivery by allowing implantation of a fertilized embryo (FIG. 1).

Figure 2:
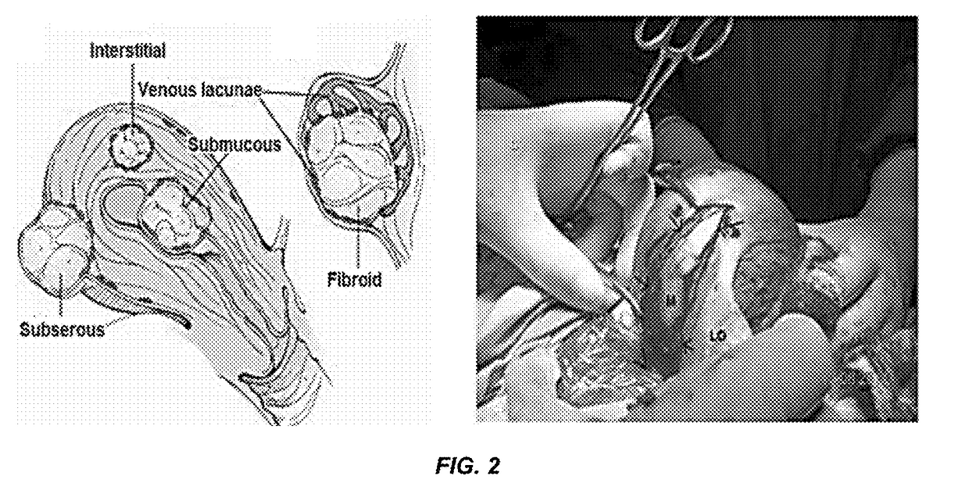
FIG. 2 illustrates uterine leiomyoma and surgical findings.

Uterine leiomyoma, commonly called uterine fibroid, is a disease that occurs in the smooth muscles of the uterus and causes excessive accumulation of extracellular matrix (ECM) to form fibroids. Uterine leiomyoma is a very prevalent disease that is found in 80% of all women in their reproductive age, and approximately 30% of women suffer from symptomatic uterine leiomyoma. Uterine leiomyoma is a cause of infertility, miscarriage, and premature labor along with menstrual pain, abnormal bleeding, and heavy periods. In particular, uterine leiomyoma may be a cause of subfertility/infertility in women of the reproductive age, and may cause menstrual pain, heavy periods, or dyspareunia. In addition, endometrial cavity-distorting uterine leiomyoma is known to have impact on endometrial implantation of a fertilized embryo as well as severe uterine leiomyoma-related symptoms, as compared with endometrial cavity non-distorting leiomyoma (FIG. 2).

The pathogenesis of uterine fibroids has not yet been elucidated, but explanations have been made for biochemical mechanisms, genetic effects, induction of normal uterine muscle transformation, etc. In particular, studies on transformation of normal muscle cells into leiomyoma are still at the early stage of genetic research, but there is also a great interest in developing new strategies for the treatment of uterine leiomyoma.

Diagnosis of uterine leiomyoma is usually done by ultrasonographic examination or radiographic examination such as CT, MRI, etc. There is no diagnostic method through a blood test. In particular, there is no technique for determining prognosis of whether or not the diagnosed uterine leiomyoma grows to induce endometrial cavity distortion. The only way is to monitor the growth process through periodic ultrasonographic examination or radiographic examination such as CT, MRI, etc.

In the case of endometrial cavity-distorting uterine fibroids, it is preferable that surgical treatment is performed before they grow as large as possible. Follow-up observations are performed every 3 to 6 months, but decision to start treatment is made only after initiation of distortion. Therefore, the criteria for the treatment decision are necessary.

Meanwhile, microRNA refers to a small size RNA having no genetic information for protein production. MicroRNA serves as a fine tuning regulator of protein production at the post-transcriptional stage, and has received much attention as an epigenetic research topic together with establishing new strategies in the area of diagnosis and treatment. However, there have been no reports of microRNA expression patterns regarding 'endometrial cavity distortion' which is of clinical significance.

Under this background, the present inventors have made extensive efforts to solve the problems above, and as a result, they developed miRNAs which may be utilized as an index capable of predicting future growth patterns of uterine leiomyoma at the time of diagnosing uterine leiomyoma, and found that miRNA may be used to identify uterine leiomyoma in need of treatment at an early stage of growth and may be used to guide treatment decisions, thereby completing the present invention.

SUMMARY OF THE INVENTION

An object of the present invention is to provide a method of treating uterine leiomyoma, the method including the steps of:

measuring a microRNA expression level in a biological sample from a subject having a likelihood of developing uterine leiomyoma;

comparing the microRNA expression level in the biological sample with a microRNA expression level in a normal control group; and administering a therapeutic agent for uterine leiomyoma to the subject or performing surgical ablation of uterine leiomyoma, when the microRNA expression level in the biological sample is downregulated, as compared with the microRNA expression level in the normal control group.

Another object of the present invention is to provide a composition for diagnosing uterine leiomyoma, the composition including an agent capable of detecting a microRNA expression level in a biological sample.

Still another object of the present invention is to provide a kit for diagnosing uterine leiomyoma, the kit including the composition for diagnosing uterine leiomyoma.

Still another object of the present invention is to provide a method of diagnosing uterine leiomyoma, the method including the steps of measuring a microRNA expression level in a biological sample from a subject; and determining that the subject has uterine leiomyoma when the microRNA expression level is downregulated, as compared with that of a normal control group.

DETAILED DESCRIPTION OF THE PREFERRED EMBODIMENTS

The present invention will be described in detail as follows. Meanwhile, each description and embodiment disclosed in this invention may also be applied to other descriptions and embodiments. That is, all combinations of various elements disclosed in this invention fall within the scope of the present invention. Further, the scope of the present invention is not limited by the specific description described below.

To achieve the objects, one aspect of the present invention provides a composition for diagnosing uterine leiomyoma, the composition including an agent capable of detecting a miRNA expression level in a biological sample.

In the present invention, the biological sample may be feces, blood, plasma, serum, lymphatic fluid, cerebrospinal fluid, isolated tissues, isolated cells, saliva, urine, etc., and more specifically, blood, but is not limited thereto. The biological sample may be an isolated biological sample.

In the present invention, miRNA (microRNA) refers to a small non-coding RNA molecule composed of about 22 nucleotides, which is found in plants, animals, viruses, etc., and known to function in RNA silencing and post-transcriptional regulation of gene expression. miRNAs are utilized in determining the incidence and extent of a disease, but they have not been utilized in diagnosing uterine leiomyoma and/or determining endometrial cavity distortion in uterine leiomyoma, which was first demonstrated by the present inventors. Further, with regard to the diagnosis of uterine leiomyoma and/or the determination of endometrial cavity distortion in uterine leiomyoma, a diagnostic method of using a simple method, such as blood sampling, etc., was first developed.

In the present invention, the diagnosis of uterine leiomyoma may be to diagnose uterine leiomyoma itself, but it may be more specifically to diagnose whether or not uterine leiomyoma is endometrial cavity-distorting uterine leiomyoma. In other words, the diagnosis of uterine leiomyoma may be to predict occurrence of endometrial cavity distortion and prognosis thereof.

In the present invention, uterine leiomyoma (leiomyosarcoma) is a disease that occurs in the smooth muscles of the uterus and causes excessive accumulation of extracellular matrix (ECM) to form fibroids. Endometrial cavity distortion which may be involved in uterine leiomyoma is known to exacerbate symptoms of uterine leiomyoma as well as to have a great influence on endometrial implantation. Therefore, with respect to the objects of the present invention, the uterine leiomyoma may be uterine leiomyoma having endometrial cavity distortion or uterine leiomyoma having a likelihood of developing endometrial cavity distortion, or uterine leiomyoma with endometrial cavity distortion. Furthermore, when uterine leiomyoma or presence of endometrial cavity distortion in uterine leiomyoma is early diagnosed through examination of the miRNA expression level by using the composition of the present invention, effective and rapid treatment is possible.

As used herein, the term "diagnosis" means identifying the presence or feature of a pathological state, progression of a disease, therapeutic effects on the diseases during treatment, etc. With respect to the objects of the present invention, the diagnosis may mean diagnosis of uterine leiomyoma itself or diagnosis of the presence of endometrial cavity distortion in uterine leiomyoma, but is not limited thereto.

Figure 3:
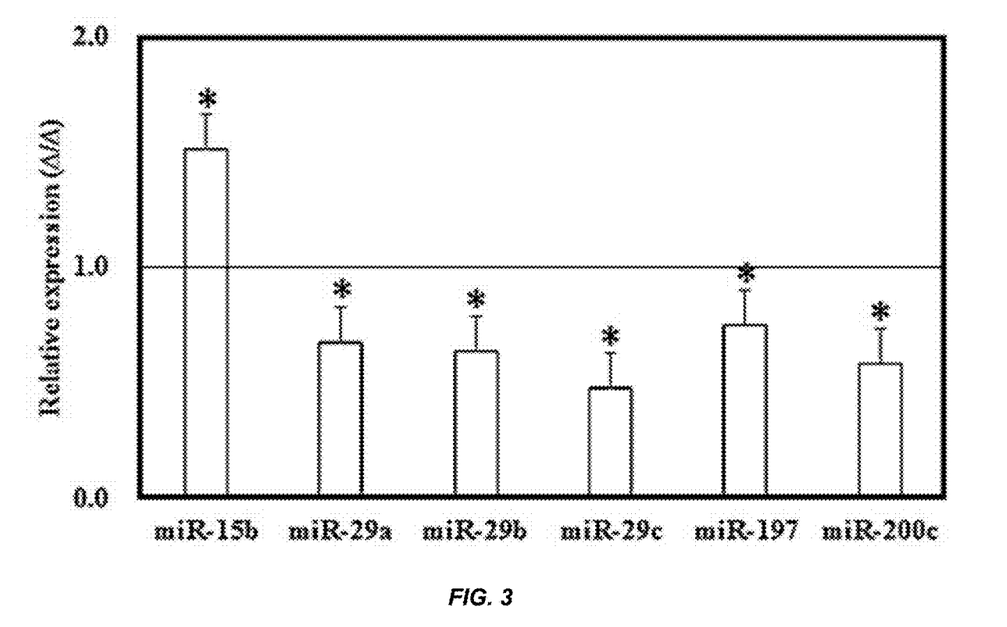
FIG. 3 shows expression levels of microRNAs in uterine leiomyoma, compared to those in normal uterine myometrium.
Figure 4A:
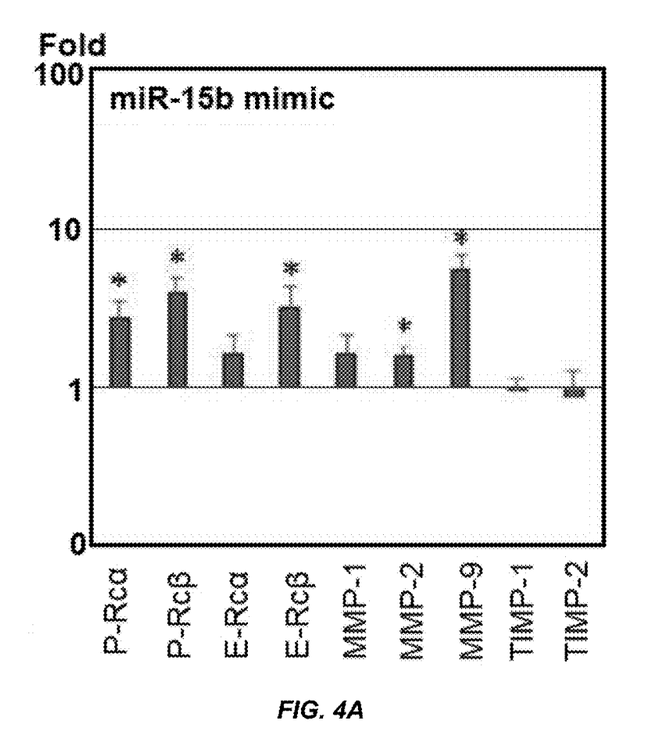
FIG. 4A-H shows expression levels of genes associated with characteristics of uterine leiomyoma by treatment with the miRNA mimics or inhibitors.
Figure 4B:
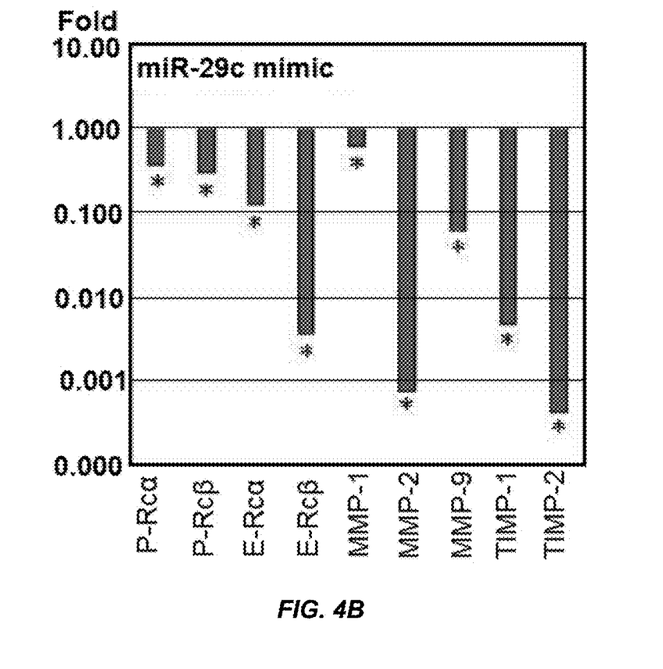
Figure 4C:
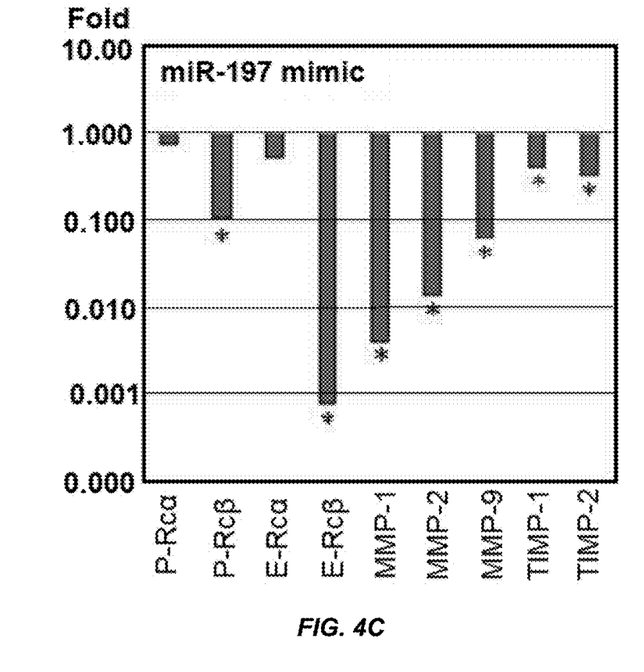
Figure 4D:
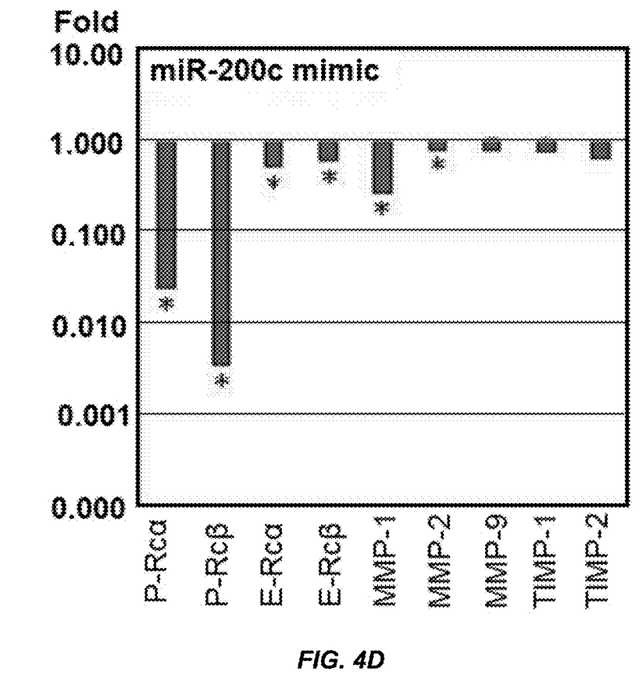
Figure 4E:
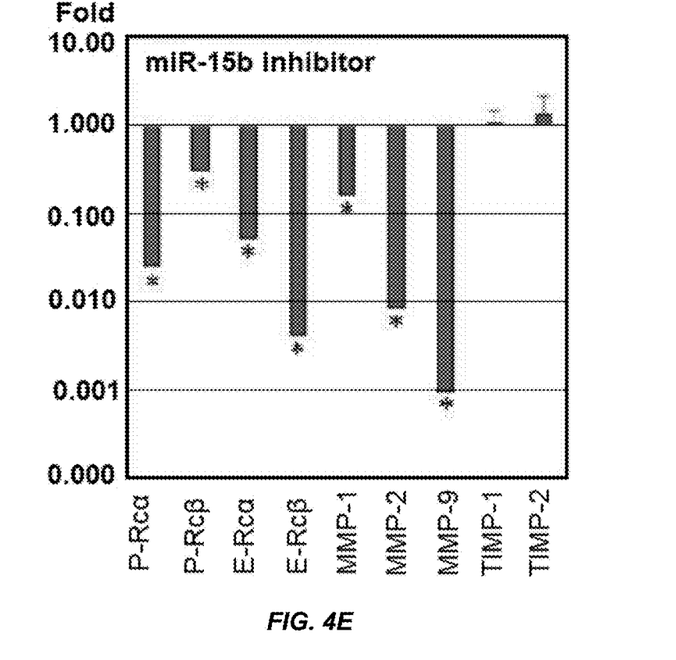
Figure 4F:
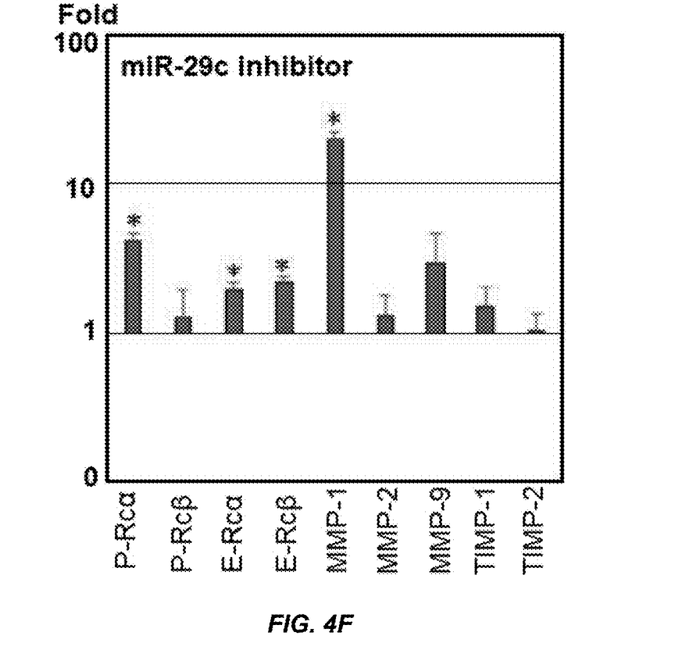
Figure 4G:
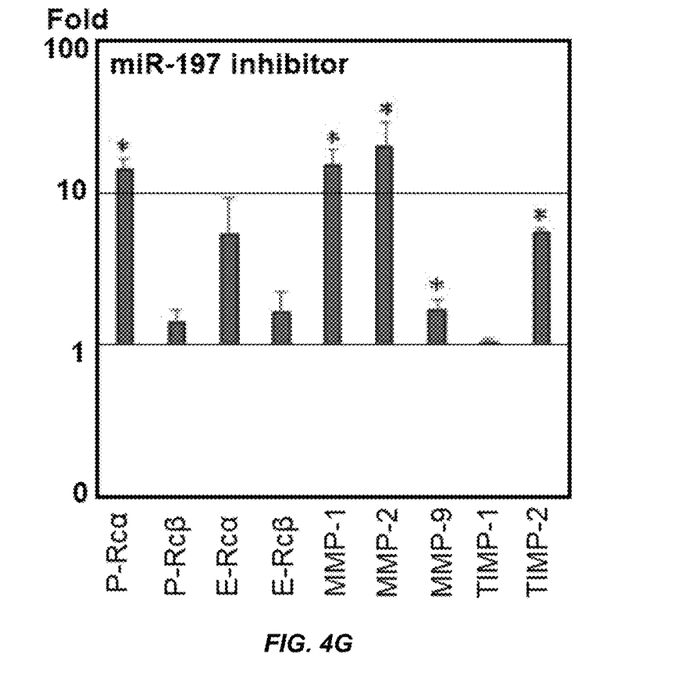
Figure 4H:
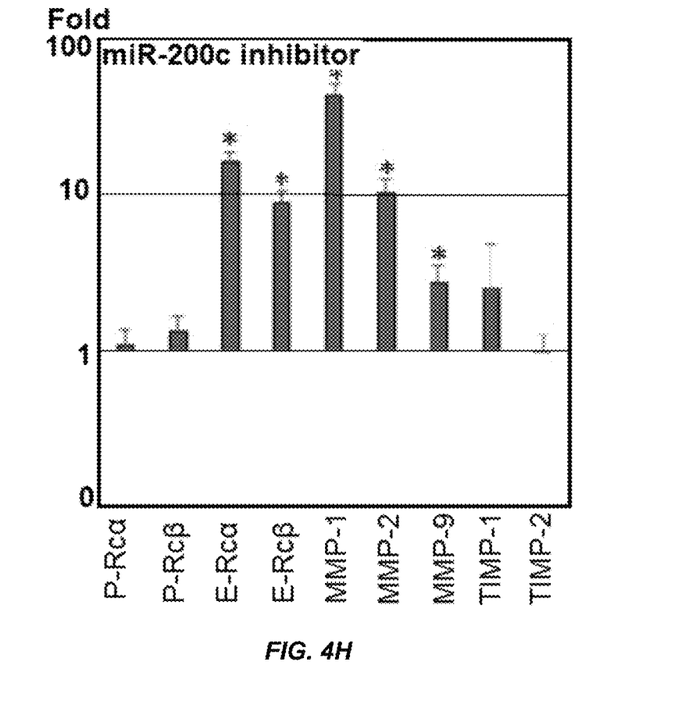

In one embodiment of the present invention, the occurrence of uterine leiomyoma and the presence of endometrial cavity distortion were analyzed through miRNA expression patterns in the uterine leiomyoma tissues. As a result, when uterine leiomyoma occurs, expression levels of microRNA-29a, microRNA-29b, microRNA-29c, microRNA-197, and microRNA-200c were found to be downregulated (FIG. 3).

Figure 5:
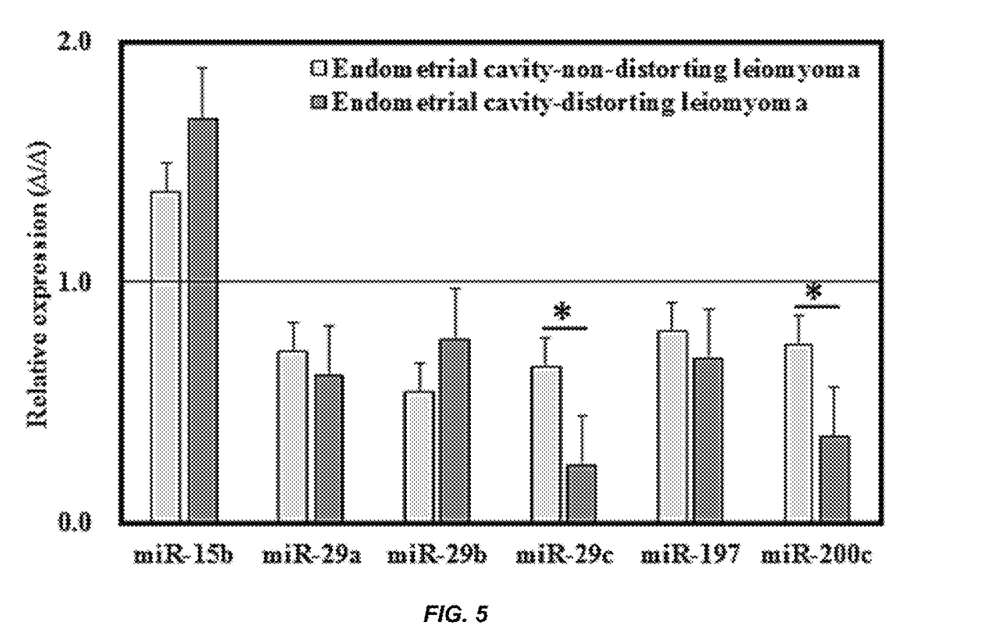
FIG. 5 shows comparison of miRNA expression levels between endometrial cavity-distorting uterine leiomyoma and endometrial cavity-non-distorting uterine leiomyoma.

It was also found that microRNA-29c and microRNA-200c expression was significantly downregulated in uterine leiomyoma with endometrial cavity distortion, as compared with uterine leiomyoma without endometrial cavity distortion (FIG. 5). Therefore, when the miRNA-29c or miRNA-200c expression level is downregulated, as compared with a normal control group, it may be diagnosed as uterine leiomyoma having endometrial cavity distortion or uterine leiomyoma having a likelihood of developing endometrial cavity distortion.

Figure 6:
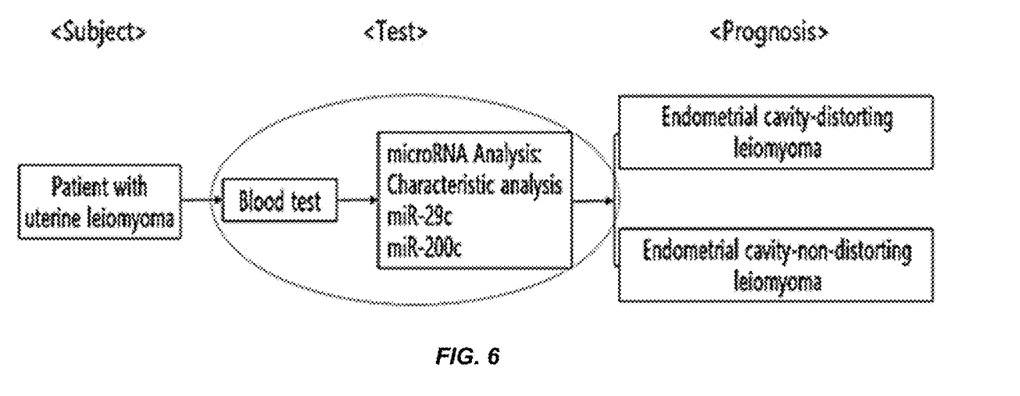
FIG. 6 shows a procedure for predicting a growth pattern of endometrial smooth muscle.

Taken together, in the present invention, the mRNA expression level in a body sample from a patient with uterine leiomyoma is analyzed and compared, thereby easily and accurately identifying the presence of endometrial cavity distortion in the patient with uterine leiomyoma (FIG. 6).

The miRNA may include any miRNA, as long as it may be used in diagnosing uterine leiomyoma and/or determining the presence of endometrial cavity distortion in uterine leiomyoma. For example, the miRNA may be miRNA selected from the group consisting of miRNA-29a, miRNA-29b, miRNA-29c, miRNA-197, and miRNA-200c, and specifically, miRNA-29c or miRNA-200c. The miRNA-29c may consist of a nucleotide sequence of SEQ ID NO: 4, and the miRNA-200c may consist of a nucleotide sequence of SEQ ID NO: 6.

In the present invention, the agent capable of detecting the miRNA expression level refers to a means used to amplify or detect the miRNA in order to identify or measure the miRNA expression level, and the agent refers to an agent used in a method of measuring a level of target miRNA in a sample. As the agent capable of detecting the miRNA expression level in a biological sample, a reagent, an agent, or an apparatus generally used in the art may be used without limitation. Specifically, the agent capable of detecting the miRNA level may be a pair of primers or a probe specifically binding to the miRNA, but is not limited thereto.

Another aspect of the present invention provides a kit for diagnosing uterine leiomyoma, the kit including the composition for diagnosing uterine leiomyoma. The uterine leiomyoma diagnosis is the same as described above.

The kit of the present invention may be used in diagnosing the presence or prognosis of endometrial cavity distortion by measuring the miRNA expression level in a tissue sample from a subject with uterine leiomyoma. The kit may include, but is not particularly limited to, a composition, a solution, or an apparatus, which includes one or more kinds of different constituents suitable for analysis methods as well as the agent for detecting miRNA.

To increase sensitivity, treatment such as centrifugation or concentration of blood may be performed.

A substrate used in the kit of the present invention may further include a chromophore for identifying the contact when being in contact with the biological sample.

To increase sensitivity and specificity, the kit may also include the case of being used in combination with existing kits for diagnosing uterine fibroid, for example, the case of being used in the form of a complex kit.

Still another aspect of the present invention provides a method of providing information for diagnosis of uterine leiomyoma or a method of diagnosing uterine leiomyoma, the method including the steps of measuring a microRNA expression level in a biological sample from a subject having a likelihood of developing uterine leiomyoma; and determining that the subject has uterine leiomyoma when the microRNA expression level is downregulated, as compared with that of a normal control group.

Still another aspect of the present invention provides a method of treating uterine leiomyoma, the method including the steps of measuring a microRNA expression level in a biological sample from a subject having a likelihood of developing uterine leiomyoma; comparing the microRNA expression level in the biological sample with a microRNA expression level in a normal control group; and administering a therapeutic agent for uterine leiomyoma to the subject or performing surgical ablation of uterine leiomyoma, when the microRNA expression level in the biological sample is downregulated, as compared with the microRNA expression level in the normal control group.

The biological sample, the microRNA, the uterine leiomyoma, and the endometrial cavity distortion are the same as described above.

Furthermore, the microRNA may be miRNA-29c or miRNA-200c, and in this case, uterine leiomyoma with endometrial cavity distortion may be diagnosed, i.e., whether or not uterine leiomyoma has endometrial cavity distortion or has a likelihood of developing endometrial cavity distortion may be diagnosed.

As used herein, the term "subject" means all animals including humans that already have uterine leiomyoma or have a likelihood of developing uterine leiomyoma. The animals may be mammals, such as cattle, horses, sheep, pigs, goats, camels, antelopes, dogs, cats, etc., which need treatment of similar symptoms, as well as humans, but are not limited thereto.

As described above, the present invention is characterized in that, after determining whether or not a subject having a likelihood of developing uterine leiomyoma actually has uterine leiomyoma, the result is used as a criterion for the treatment decision.

Specifically, when the microRNA expression level in the biological sample is downregulated, as compared with the microRNA expression level in the normal control group, it may be determined as developing uterine leiomyoma, specifically, uterine leiomyoma with endometrial cavity distortion. Further, when uterine leiomyoma is diagnosed as uterine leiomyoma having endometrial cavity or uterine leiomyoma having a likelihood of developing endometrial cavity distortion, it is determined as uterine leiomyoma that needs to be treated. In this case, treatment decision of uterine leiomyoma may be made, and accordingly, a therapeutic agent for uterine leiomyoma may be administered to the subject or surgical ablation of uterine leiomyoma may be performed.

The treatment of uterine leiomyoma may be performed by a known therapeutic method, but is not limited thereto. For example, an anticancer agent may be used as the therapeutic agent, or radiation therapy may be performed, or surgical ablation of uterine leiomyoma may be performed.

Hereinafter, the present invention will be described in more detail with reference to Examples. However, these Examples are for illustrative purposes only, and the scope of the present invention is not intended to be limited by these Examples.

Example 1: Measurement and Comparison of miRNA Expression Level in Uterine Leiomyoma Tissue The presence or absence of endometrial cavity distortion was analyzed through miRNA expression patterns of uterine leiomyoma tissues.

In detail, microRNA expression levels were examined in 15 cases of endometrial cavity-distorting leiomyoma and 11 cases of endometrial cavity-non-distorting leiomyoma. The microRNAs targeted for the detection of expression levels were microRNA-15b, -29a, -29b, -29c, -197, and -200c. Sequences of the microRNAs are as in Table 1 below, respectively.

TABLE 1

| microRNA | Sequence | SEQ ID NO. |
|---|---|---|
| miR-15b | tagcagcacatcatggtttaca | SEQ ID NO: 1 |
| miR-29a | tagcaccatctgaaatcggtt | SEQ ID NO: 2 |
| miR-29b | tagcaccatttgaaatcagtgtt | SEQ ID NO: 3 |
| miR-29c | tagcaccatttgaaatcggt | SEQ ID NO: 4 |
| miR-197 | ttcaccaccttctccacccagc | SEQ ID NO: 5 |
| miR-200c | taatactgccgggtaatgatgga | SEQ ID NO: 6 |

The uterine leiomyoma tissues obtained during surgery were cut into 1 cm×1 cm pieces, and homogenized using a surgical blade. The tissue pieces were collected, and HBSS was removed, and Trizol (Invitrogen) was added thereto to extract RNAs. The extracted RNAs were quantified, and quantity of the RNA extracted from each sample was normalized to 0.5 μg, and then reverse-transcribed for cDNA synthesis using an Express SYBR® Green ERTM kit (Invitrogen). After reverse-transcription, miRNA expression was analyzed using a miScript II RT Kit (Qiagen).

As shown in FIG. 3, microRNA expression levels in uterine leiomyoma were examined, as compared with those in normal uterine myometrium, and as a result, the expression level of microRNA-15b was upregulated (>1.0), whereas the expression levels of other microRNAs, microRNA-29a, -29b, -29c, -197, and 200c were downregulated (<1.0).

Therefore, it can be seen that when uterine leiomyoma develops, expression levels of microRNA-29a, -29b, -29c, -197, and 200c are downregulated, and the corresponding microRNAs may be used in diagnosing uterine leiomyoma.

Example 2: Examination of Changes in Gene Expression by Using miRNA Mimics or Inhibitors miRNAs significant in the diagnosis of uterine leiomyoma were identified in Example 1. In this regard, mimics or inhibitors of the corresponding miRNAs were transfected into uterine leiomyoma cells to examine expression regulation of genes associated with characteristics of uterine leiomyoma.

Homogenized uterine leiomyoma pieces were collected and treated with 1 mg/ml of collagenase I (Invitrogen) and allowed to react for 1 hour at 37° C. The reacted tissue pieces were filtered through a 70 μm cell strainer, and then centrifuged at 3,000 rpm. The collected cells were suspended in a culture medium, and adhered to a culture dish. The culture medium was composed of DMEM/F12 without phenol red, 20% fetal bovine serum (FBS), 1% insulin-transferrin-selenium (ITS), and 50 U/ml penicillin-streptomycin (all purchased from Invitrogen), and replaced every other day.

It was examined whether or not expression of genes associated with characteristics of uterine leiomyoma was changed by transfection of mimics or inhibitors of microRNA-15b, microRNA-29c, microRNA-197, and microRNA-200c into uterine leiomyoma cells. 48 hours after transfection of 10 μM of miR-200c mimics or inhibitors into the cultured uterine leiomyoma cells, the cells were collected, and changes in the expression patterns of miRNA and target genes (Progesterone receptor (P-Rc) α, P-Rc β, Estrogen (E)-Rc α, E-Rcβ, matrix metalloproteinase (MMP)-1, -2, -9, tissue inhibitors of metalloproteinases (TIMP)-1, TIMP-2) were analyzed by qPCR.

As a result, it was confirmed that microRNA-15b expression was upregulated by treatment with the mimics, and downregulated by treatment with the inhibitors, whereas microRNA-29c, microRNA-197, and microRNA-200c expression was downregulated by treatment with the mimics, and upregulated by treatment with the inhibitors (FIG. 4).

These results, consistent with the results of Example 1, indicate that microRNA-29c, microRNA-197 and microRNA-200c may be used in diagnosing uterine leiomyoma.

Example 3: Examination of miRNA for Diagnosis of Endometrial Cavity-Distorting Uterine Leiomyoma The microRNAs for the diagnosis of uterine leiomyoma itself were selected in Examples 1 and 2. To examine that the microRNAs may also be used in diagnosing endometrial cavity-distorting uterine leiomyoma, expression levels of the miRNAs in endometrial cavity-distorting uterine leiomyoma and endometrial cavity-non-distorting leiomyoma were analyzed and compared by RT-PCR. The experimental method was performed in the same manner as in Example 1.

As a result, as shown in FIG. 5, it was confirmed that microRNA-29c and microRNA-200c expression was significantly downregulated in endometrial cavity-distorting uterine leiomyoma, as compared with endometrial cavity-non-distorting leiomyoma. Meanwhile, it was confirmed that although expression levels of miRNAs other than microRNA-29c and microRNA-200c were upregulated or downregulated, they were not significant.

Take together, the above results suggest that the presence or possibility of endometrial cavity distortion in a patient with uterine leiomyoma may be readily and accurately identified by analyzing and comparing miRNA expression levels in a body sample, e.g., a blood sample from the patient with uterine leiomyoma, as shown in FIG. 6.

Accordingly, future growth patterns of uterine leiomyoma may be predicted at an early stage of growth, which may guide treatment decisions.

Based on the above description, it will be understood by those skilled in the art that the present invention may be implemented in a different specific form without changing the technical spirit or essential characteristics thereof. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds are therefore intended to be embraced by the claims.

Effect of the Invention

From a medical point of view, it is very important to develop indices that may guide treatment decisions by predicting future growth patterns at the early stage of uterine leiomyoma. In addition, with increasing infertility rates, there are increasing societal demands for the indices for early diagnosis of endometrial cavity-distorting uterine leiomyoma which is one of the causes of infertility.

In the situation the indices capable of accurately predicting growth patterns of uterine leiomyoma through a blood test have not been developed, the present invention provides microRNAs which are indices capable of predicting future growth patterns of uterine leiomyoma at the time of diagnosing uterine leiomyoma, and thus uterine leiomyoma that needs to be treated may be identified at the early stage, thereby being used in making treatment decisions.

What is claimed is:

1. A method of treating endometrial cavity-distorting uterine leiomyoma, the method comprising the steps of:
   measuring a microRNA expression level in a uterine leiomyoma sample from a subject having a likelihood of developing endometrial cavity-distorting uterine leiomyoma, wherein the microRNA is miRNA-29c or miRNA-200c;
   comparing the microRNA expression level in the uterine leiomyoma sample with a microRNA expression level in a control endometrial cavity non-distorting uterine leiomyoma sample;
   determining that the microRNA expression level in the uterine leiomyoma sample is downregulated as compared to the microRNA expression level in the control endometrial cavity non-distorting uterine leiomyoma sample and that the subject has endometrial cavity-distorting uterine leiomyoma; and
   performing surgical ablation of the endometrial cavity-distorting uterine leiomyoma.

2. The method of claim 1, wherein the measuring of the microRNA expression level is performed by using an agent capable of detecting the microRNA expression level.

3. The method of claim 2, wherein the agent is one or more agents selected from the group consisting of a pair of primers or a probe specifically binding to the microRNA.

4. The method of claim 1, wherein the miRNA-29c consists of a nucleotide sequence of SEQ ID NO: 4.

5. The method of claim 1, wherein the miRNA-200c consists of a nucleotide sequence of SEQ ID NO: 6.

\* \* \* \* \*